(12) United States Patent
de los Rios et al.

(10) Patent No.: US 7,964,196 B2
(45) Date of Patent: Jun. 21, 2011

(54) SELF-ASSEMBLING NANOPARTICLE DRUG DELIVERY SYSTEM

(75) Inventors: Miguel de los Rios, Ventura, CA (US); Kenneth J. Oh, Santa Barbara, CA (US)

(73) Assignee: Chimeros, Inc., San Diego, CA (US)

( * ) Notice: Subject to any disclaimer, the term of this patent is extended or adjusted under 35 U.S.C. 154(b) by 550 days.

(21) Appl. No.: 11/138,593

(22) Filed: May 25, 2005

(65) Prior Publication Data

US 2006/0292174 A1     Dec. 28, 2006

Related U.S. Application Data

(60) Provisional application No. 60/574,409, filed on May 25, 2004.

(51) Int. Cl.
*A61K 39/29* (2006.01)
*A61K 39/385* (2006.01)
*C07K 14/02* (2006.01)

(52) U.S. Cl. ............. 424/189.1; 424/194.1; 424/196.11; 424/201.1; 424/202.1; 424/227.1; 424/192.1; 530/350; 530/402; 977/795; 977/797; 977/798; 977/800; 977/801; 977/802

(58) Field of Classification Search .................. None
See application file for complete search history.

(56) References Cited

U.S. PATENT DOCUMENTS

| | | | |
|---|---|---|---|
| 5,133,961 A | 7/1992 | Ellis et al. | |
| 5,420,026 A | 5/1995 | Payne | |
| 5,439,686 A | 8/1995 | Desai et al. | |
| 5,498,421 A | 3/1996 | Grinstaff et al. | |
| 5,620,689 A * | 4/1997 | Allen et al. | 424/178.1 |
| 5,670,630 A | 9/1997 | Thill | |
| 5,714,316 A | 2/1998 | Weiner et al. | |
| 5,858,726 A | 1/1999 | Payne | |
| 5,863,541 A | 1/1999 | Samulski et al. | |
| 5,980,901 A | 11/1999 | Shih et al. | |
| 6,046,173 A | 4/2000 | Forstova et al. | |
| 6,063,370 A | 5/2000 | Dadey | |
| 6,096,331 A | 8/2000 | Desai et al. | |
| 6,204,059 B1 | 3/2001 | Samulski et al. | |
| 6,231,864 B1 * | 5/2001 | Birkett | 424/189.1 |
| 6,387,662 B1 | 5/2002 | Liang et al. | |
| 6,420,160 B1 | 7/2002 | Bloch | |
| 6,506,405 B1 | 1/2003 | Desai et al. | |
| 6,506,559 B1 | 1/2003 | Fire et al. | |
| 6,537,579 B1 | 3/2003 | Desai et al. | |
| 6,573,009 B1 | 6/2003 | Noda et al. | |
| 6,602,706 B1 | 8/2003 | Fallaux et al. | |
| 6,602,932 B2 | 8/2003 | Feldheim et al. | |
| 6,616,944 B2 | 9/2003 | Kissel et al. | |
| 6,620,617 B1 | 9/2003 | Mathiowitz et al. | |
| 6,627,202 B2 | 9/2003 | Murray | |
| 6,696,038 B1 | 2/2004 | Mahato et al. | |
| 6,710,173 B1 | 3/2004 | Binley et al. | |
| 6,749,868 B1 | 6/2004 | Desai et al. | |
| 6,753,006 B1 | 6/2004 | Desai et al. | |
| 6,984,386 B2 | 1/2006 | Douglas et al. | |
| 7,056,704 B2 | 6/2006 | Tuschl et al. | |
| 7,078,194 B2 | 7/2006 | Withers et al. | |
| 7,101,995 B2 | 9/2006 | Lewis et al. | |
| 7,282,199 B2 | 10/2007 | Gao et al. | |
| 7,332,321 B2 | 2/2008 | Belcher et al. | |
| 7,332,337 B2 | 2/2008 | van Es et al. | |
| 7,344,872 B2 | 3/2008 | Gao et al. | |
| 7,422,902 B1 | 9/2008 | Wheeler et al. | |
| 2004/0005338 A1 | 1/2004 | Bachmann et al. | |
| 2004/0247660 A1 | 12/2004 | Singh | |
| 2005/0004002 A1 | 1/2005 | Desai et al. | |
| 2005/0089526 A1 | 4/2005 | Moore et al. | |
| 2006/0292118 A1 | 12/2006 | Kuroda et al. | |
| 2006/0292174 A1 | 12/2006 | de los Rios et al. | |
| 2007/0248573 A1 | 10/2007 | Sturino | |
| 2007/0249554 A1 | 10/2007 | Tuszynski | |
| 2007/0258889 A1 | 11/2007 | Douglas et al. | |
| 2007/0269370 A1 | 11/2007 | Davis et al. | |
| 2007/0280962 A1 | 12/2007 | Murray | |
| 2008/0050343 A1 | 2/2008 | Wilson et al. | |
| 2008/0050345 A1 | 2/2008 | Wilson et al. | |
| 2008/0069802 A1 | 3/2008 | Davis et al. | |
| 2008/0075737 A1 | 3/2008 | Gao et al. | |
| 2008/0075740 A1 | 3/2008 | Gao et al. | |
| 2008/0090281 A1 | 4/2008 | Wilson et al. | |
| 2008/0125385 A1 | 5/2008 | Hajjar et al. | |
| 2008/0131928 A1 | 6/2008 | Handa et al. | |
| 2009/0226525 A1 | 9/2009 | de los Rios et al. | |

FOREIGN PATENT DOCUMENTS

| | | |
|---|---|---|
| EP | 0863987 B1 | 9/1998 |
| EP | 0920514 B1 | 6/1999 |
| EP | 1204761 B1 | 5/2002 |
| EP | 1219705 A1 | 7/2002 |
| EP | 1447079 A1 | 8/2004 |
| EP | 1563834 | 8/2005 |
| EP | 1845163 A2 | 10/2007 |
| EP | 1849799 A1 | 10/2007 |
| EP | 1944043 A1 | 7/2008 |

(Continued)

OTHER PUBLICATIONS

Jenny R et al. "Acritical review of the methods for cleavage of fusion proteins with thrombin and factor Xa" Protein Expression and Purification 31(2-3):1-11, 2003, cited in IDS).*

(Continued)

*Primary Examiner* — Bo Peng

(74) *Attorney, Agent, or Firm* — Goodwin Procter, LLP

(57) ABSTRACT

A self-assembling nanoparticle drug delivery system for the delivery of drugs including peptides, proteins, nucleic acids or synthetic chemical drugs is provided. The self-assembling nanoparticle drug delivery system described herein includes viral capsid proteins, such as Hepatitis B Virus core protein, encapsulating the drug, a lipid bi-layer envelope and targeting or facilitating molecules anchored in the lipid bilayer. A method for construction of the self-assembling nanocparticle drug delivery system is also provided.

15 Claims, 5 Drawing Sheets

FOREIGN PATENT DOCUMENTS

| | | | |
|---|---|---|---|
| WO | WO-95/32706 A1 | 12/1995 | |
| WO | WO 99/40214 | * | 2/1999 |
| WO | 9940214 | 8/1999 | |
| WO | 0009158 | 2/2000 | |
| WO | 0102551 | 1/2001 | |
| WO | WO-01/12235 A2 | 2/2001 | |
| WO | 0244204 | 6/2002 | |
| WO | 2004047812 | 6/2004 | |
| WO | WO-2006/033679 A2 | 3/2006 | |
| WO | WO-2006/066048 A2 | 6/2006 | |
| WO | WO-2007/126764 A2 | 11/2007 | |
| WO | WO-2007/136263 A1 | 11/2007 | |
| WO | WO-2008/008881 A1 | 1/2008 | |
| WO | WO-2008/010864 A2 | 1/2008 | |
| WO | WO-2008/021908 A2 | 2/2008 | |
| WO | WO-2008/024427 A2 | 2/2008 | |
| WO | WO-2008/027084 A2 | 3/2008 | |
| WO | WO-2008/037504 A1 | 4/2008 | |
| WO | WO-2008/048288 A2 | 4/2008 | |
| WO | WO-2008/051101 A1 | 5/2008 | |
| WO | WO-2008/054826 A2 | 5/2008 | |
| WO | WO-2008/124165 A2 | 10/2008 | |

OTHER PUBLICATIONS

Lundstrom K et al. "Breakthrough in cancer therapy:encapsulation of drugs and viruses" Curr. Drug Disc (2002) Nov. 19-23, Cited in IDS.*

Moghimi SM et al. "Long-circulating and target-specific nanoparticles: theory to practice" Pharmarceutical Review, 53(2):283-318, 2001, cited in IDS.*

Moreira J. et al. "Use of the post-insertion technique to insert peptide ligands into pre-formed Stealth liposomes with retention of binding activity and cytotoxicity" Pharmaceutical Research 19(3):265-269, 2002.*

Scott MD, et al. "Chemical camouflage of antigenic determinants: stealth erythrocytes" Proc Natl Acad Sci U S A. Jul. 8, 1997;94(14):7566-71.*

Yamada, T. et al., "Nanoparticles for the Delivery of Genes and Drugs to Human Hepatocytes", Nature Biotechnology, vol. 21, No. 8, 2003, pp. 885-890.

Boisgerault F et al. "Virus-like particles: a new family of delivery systems." Expert Rev. Vaccines 1(1):101-9, 2002.

Brunfield S et al. "Heterologous expression of the modified coat protein of Cowpea chlorotic mottle bromovirus results in the assembly of protein cages with altered architecture and function." J Gen Virol 85:1049-1053, 2004.

Crommelin Dja et al. "Nanotechnological approaches for the delivery of macromolecules." J Controlled Release 87:81-88, 2003.

Haag R. "Supramolecular drug-delivery systems based on polymeric core-shell architectures." Angew Chem Int Ed 43:278-282, 2004.

Jenny RJ et al. "A critical review of the methods for cleavage of fusion proteins with thrombin and factor Xa." Prot Express Purif 31:1-11, 2003.

Kayser O et al. "Formulation and biopharmaceutical issues in the development of drug delivery systems for antiparasitic drugs." Parasitol Res 90:S63-S70, 2003.

Liu J et al. "Nanostructured materials designed for cell binding and transduction." Biomacromolecules 2:362-368, 2001.

Lundstrom K et al. "Breakthrough in cancer therapy: encapsulation of drugs and viruses." Curr Drug Disc : Nov. 2002, pp. 19-23.

Managit C et al. "Targeted and sustained drug delivery using PEGylated galatosylated liposomes." Int J Pharmaceutics 266:77-84, 2003.

Moghimi SM et al. "Long-circulating and target-specific nanoparticles: theory to practice." Pharmacol Rev 53:283-318, 2001.

Sahoo SK et al. "Nanotech approaches to drug delivery and imaging." Drug Disc Today 8:1112-1120, 2003.

Schmidt U et al. "Protein and peptide delivery via engineered polyomavirus-like particles." FASEB J 15:1646-1648, 2001.

Schmidt U et al. "Binding of external ligands onto an engineered virus capsid." Protein Eng 14:769-774, 2001.

Sinha VR et al. "Biodegradable microspheres for protein delivery." J Controlled Rel 90:261-280, 2003.

Rocco MC et al. "Social Implications of Nanoscience and Technology." National Science Foundation Report, 2001.

Panyam J et al. "Biodegradable nanoparticles for drug and gene delivery to cells and tissue." Adv Drug Del Rev 55:329-47, 2003.

Lamprecht et al. "Biodegradable nanoparticles for targeted drug delivery in treatment of inflammatory bowel disease." J Pharmacol Exp Ther 299:775-81, 2002.

Monsky WL et al. "Augmentation of transvascular transport of macromolecules and nanoparticles in tumors using vascular endothelial growth factor." Cancer Res. 59:4129-35, 1999.

Panyam J et al. "Fluorescence and electron microscopy probes for cellular and tissue uptake of poly(D,L-lactide-coglycolide) nanoparticles." Int J Pharm 262:1-11, 2003.

Maeda H "The enhanced permeability and retention (EPR) effect in tumor vasculature: the key role of tumor-selective macromolecular drug targeting." Adv Enzyme Regul 41:189-207, 2001.

Sahoo SK et al. "Pegylated zinc protoporphyrin: a water-soluble heme oxygenase inhibitor with tumor targeting capacity." Bioconjugate Chem 13:1031-8, 2002.

Crowther RA et al. "Three-dimensional structure of hepatitis B virus core particles determined by electron cryomicroscopy." Cell 77:943-50, 1994.

Bottcher B et al. "Determination of the fold of the core protein of hepatitis B virus by electron cryomicroscopy." Nature 386:88-91, 1997.

Wynne SA et al. "The crystal structure of the human hepatitis B virus capsid." Molecular Cell 3:771-80, 1999.

Martin FJ et al. "Immunospecific targeting of liposomes to cells: a novel and efficient method for covalent attachment of Fab' fragments via disulfide bonds." Biochemistry 20:4229-38, 1981.

de Kruif et al. "Biosynthetically lipid-modified human scFv fragments from phage display libraries as targeting molecules for immunoliposomes" FBBS Lett. Dec. 16, 1996;399(3):232-6.

DeNardo et al. "Efficacy and Toxicity of 67Cu-2IT-BAT-Lym-1 Radio-immunoconjugate in Mice Implanted with Human Burkitt's Lymphoma (Raji)" Cln. Cancer Res., 3:71-79 (1997).

Fasbender et al. "Complexes of Adenovirus with Polycationic Polymers and Cationic Lipids Increase the Efficiency of Gene Transfer in Vitro and Vivo" J. Biol. Chem, 272(10):6479-6489, 1997.

Fernandez et al. "Activated protein C Correlates Inversely with Thrombin Levels in Resting Healthy Individuals" Am. J. Hematol., 56:29-31 (1997).

Hashida et al. "Fusion of HIV-1 Tat protein transduction domain to poly-lisine as a new DNA delivery tool" British J. of Cancer, Nature Publ. Group., London, GB, vol. 90, No. 6, pp. 1252-1258, 2004.

International Search Report for PCT/US05/18456, dated Sep. 13, 2006.

International Search Report for PCT/US08/08938, dated Oct. 18, 2007.

International Search Report for PCT/US08/04585, dated Mar. 17, 2009.

Larsen et al. "Lymphoproliferative disorders: prospects for gene therapy" Pathology 2005 (Dec;37(6):523-33.

Mansfield et al. "Recombinant RFB4 Immunotoxins Exhibit Potent Cytotoxic Activity for CD22-Bearing Cells and Tumors" Blood, Sep. 1, 1997;90(5):2020-6.

Paddison et al. "Stable Expression of Gene Suppression by RNAi in mammalian cells" PNAS, vol. 99, No. 3, pp. 1443-1448.

Perales et al. "An evaluation of receptor-mediated gene transfer using synthetic DNA-ligand complexes" European J of Biochemistry, Berlin, vol. 226, No. 2, pp. 255-266, 1994.

Stevens "The cost and value of three-dimensional protein structure" Drug Disc. World 4, 4:35-48 (2003).

Wagner et al. "Transferrin-polycation-DNA complexes: The effect of polycations on the structure of the complex and DNA delivery to cells" Proceedings of the National Academy of Science of USA, Nat'l Acad. of Sci., vol. 88, No. 10, pp. 4255-4259, 1991.

Zlotnick "Are weak protein-protein interactions the general rule in capsid assembly?" Virology, 315:269-274 (2003).

* cited by examiner

SEQUENCE LISTING

```
<160> NUMBER OF SEQ ID NOS: 5

<210> SEQ ID NO 1
<211> LENGTH: 183
<212> TYPE: PRT
<213> ORGANISM: Hepatitis B virus

<400> SEQUENCE: 1

Met Asp Ile Asp Pro Tyr Lys Glu Phe Gly Ala Ser Val Glu Leu Leu
1               5                   10                  15
```

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 2
<211> LENGTH: 183
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 3
<211> LENGTH: 12

```
<212> TYPE: PRT
<213> ORGANISM: Hepatitis B virus

<400> SEQUENCE: 3

Gly Pro Gly Ala Pro Gly Leu Val Pro Arg Gly Ser
1               5                   10

<210> SEQ ID NO 4
<211> LENGTH: 12
<212> TYPE: PRT
<213> ORGANISM: Hepatitis B virus

<400> SEQUENCE: 4

Gly Pro Ala Ser Gly Pro Gly Ile Glu Gly Arg Ala
1               5                   10

<210> SEQ ID NO 5
<211> LENGTH: 23
<212> TYPE: PRT
<213> ORGANISM: Hepatitis B virus

<400> SEQUENCE: 5

Cys Ala Arg Gly Ala Arg Gly Ala Arg Gly Ala Arg Gly Ile Leu Gly
1               5                   10                  15

Val Phe Ile Leu Leu Tyr Met
            20
```

SELF-ASSEMBLING NANOPARTICLE DRUG DELIVERY SYSTEM

RELATED APPLICATIONS

This application claims the benefit of priority under 35 U.S.C. §119(e) of U.S. Provisional Patent Application No. 60/574,409 filed May 25, 2004.

FIELD OF THE INVENTION

The present invention relates to methods for drug delivery. Specifically, the present invention relates to a self-assembling drug delivery system comprised of pharmacologic drugs captured within viral capsid proteins and encapsulated in a lipid envelope.

BACKGROUND OF THE INVENTION

Nanotechnology, the term derived from the Greek word nano, meaning dwarf, applies the principals of both physical and biological sciences at a molecular or submicron level. The materials at nanoscale can be a device or system, or supramolecular structures, complexes or composites. Nanotechnology is making significant advances in biomedical applications, including drug delivery techniques.

The development of drug delivery systems for small molecules, proteins and DNA have been greatly influenced by nanotechnology. Novel drug delivery techniques are an important strategic tool for expanding drug markets. Improved drug delivery systems can address issues associated with currently used drugs such as increasing efficacy or improving safety and patient compliance (Rocco M C and Bainbridge W S, eds Social Implications of Nanoscience and Technology, National Science Foundation Report, 2001). In addition, this technology permits the delivery of drugs that are highly insoluble or unstable in biological environments. It is expected that novel drug delivery systems can make a significant contribution to the pharmaceutical market. Approximately 13% of the current global pharmaceutical market is sales of products incorporating a drug delivery system. The demand for drug delivery systems in the United States alone is expected to grow nearly 9% annually to more that US$82 billion (Rocco M C and Bainbridge W S, eds, Converging Technologies for Improving Human Performance, National Science Foundation and Department of Commerce Report, Kluwer Academic Publishers, 2002).

Many therapeutic agents have not been successful because of their limited ability to reach the target tissue. In addition, new delivery systems for anti-cancer agents, hormones, proteins, peptides and vaccines are necessary because of safety and efficacy problems with conventional administration modalities. For example, cytotoxic cancer drugs can damage both malignant and normal cells. A drug delivery system that targets the drug to the malignant tumor would decrease bystander toxicity. Protein and DNA drugs must be administered intravenously due to their instability at the high pH in the stomach after oral administration. Additional problems include premature loss of efficacy due to rapid clearance and metabolism. Drug delivery systems that can deliver protein, nucleic acid or unstable small molecules are highly desirable and are currently the subject of ongoing, and as yet unsuccessful, research.

There has been considerable research into developing biodegradable nanoparticles as effective drug delivery systems (Panyam J et al., Biodegradable nanoparticles for drug and gene delivery to cells and tissue, Adv Drug Deliv Rev. 55:329-47, 2003). Nanoparticles are solid, colloidal particles consisting of macromolecular substances that vary in size from 10-1000 nanometers. The drug of interest is either dissolved, entrapped, adsorbed, attached or encapsulated into the nanoparticle matrix. The nanoparticle matrix can be comprised of biodegradable materials such as polymers or proteins. Depending on the method of preparation, nanoparticles can be obtained with different properties and release characteristics for the encapsulated therapeutic agents (Sahoo S K and Labhasetwar V, Nanotech approaches to drug delivery and imaging, DDT 8:1112-1120, 2003).

The advantages of using nanoparticles for drug delivery result from their two main properties. First, nanoparticles, because of their small size, can penetrate through smaller capillaries and are taken up by cells, which allows efficient drug accumulation at the target sites (Panyam J et al., Fluorescence and electron microscopy probes for cellular and tissue uptake of poly (D,L-lactide-co-glycolide) nanoparticles, Int J Pharm. 262:1-11, 2003). Second, the use of biodegradable materials for nanoparticle preparation allows sustained drug release within the target site over a period of days or even weeks. Nanoparticles can also be effective drug delivery mechanisms for drugs whose targets are cytoplasmic.

Targeted delivery of nanoparticles can be achieved by either passive or active targeting. Active targeting of a therapeutic agent is achieved by conjugating the therapeutic agent or the carrier system to a tissue or cell-specific ligand (Lamprecht et al., Biodegradable nanoparticles for targeted drug delivery in treatment of inflammatory bowel disease, J Pharmacol Exp Ther. 299:775-81, 2002). Passive targeting is achieved by coupling the therapeutic agent to a macromolecule that passively reaches the target organ (Monsky W L et al., Augmentation of transvascular transport of macromolecules and nanoparticles in tumors using vascular endothelial growth factor, Cancer Res. 59:4129-35, 1999). Drugs encapsulated in nanoparticles or drugs coupled to macromolecules such as high molecular weight polymers passively target tumor tissue through the enhanced permeation and retention effect (Maeda H, The enhanced permeability and retention (EPR) effect in tumor vasculature: the key role of tumor-selective macromolecular drug targeting, Adv Enzyme Regul. 41:189-207, 2001; Sahoo SK et al., Pegylated zinc protoporphyrin: a water-soluble heme oxygenase inhibitor with tumor-targeting capacity, Bioconjugate Chem. 13:1031-8, 2002).

As macromolecules such as proteins and nucleic acids play a larger role in the therapy of disease and traditional pharmaceutical small molecules are abandoned during development due to their inability to effectively reach their intended target, improved drug delivery systems are needed. The delivery of a wide variety of drugs is hindered because they have difficulty crossing the blood brain barrier. A characteristic function of nanoparticles is their ability to deliver drugs across biological barriers to the target site and to protect the drugs from the biological environment until they reach the target site. Therefore, the use of nanoparticle delivery systems is a promising way to improve the delivery of a wide variety of bioactive agents.

SUMMARY OF THE INVENTION

The present invention provides for a novel nanoparticle drug delivery system that can be administered across mucosal barriers and is able to transport a wide range of molecules including therapeutic proteins into the circulatory system. The nanoparticles of the present invention comprise building blocks re-engineered from natural proteins self-assemble to form nanocages. During the assembly process, drugs of choice will be captured by the specific chemistries of the inward facing surfaces of the cage-forming blocks by simple diffusion/concentration mechanics. The assembled cage has special functionalities to guide the assembly of a surrounding envelope, which is an encapsulating self-assembling double layer of neutral, anionic or cationic lipids. Peptides that facilitate membrane transduction will be integrated into the lipid bi-layer envelope to endow the system with the ability to pass through cell walls. Polyethylene glycol (PEG) of varying chain lengths will next be anchored into the membrane for the purpose of eluding the immune system and to fend off attacking degradative enzymes. This multilayered delivery system orchestrates a complex arrangement of biomolecules and is entirely self-assembling. The nanoparticle drug delivery system can by administered by any route including, but not limited to, subcutaneous, intravenous and intramuscular routes and passage through a mucosal layer such as oral, transdermal, intranasal and buccal routes.

The present invention represents a synthetically enveloped non-viral capsule composed of re-engineered biological molecules and enhanced with synthetic chemical components. Although this design is inspired by the natural behavior of viruses, this system is non-replicating. In addition, all of the proteins used to make the building blocks of the system were all re-engineered to exhibit desired characteristics by altering stabilities and removing or adding disulfide linkages. The building blocks are designed so that once the cage starts to disintegrate, they are degraded quickly so as to limit any potential immune response. A characteristic of this drug delivery system is its ability to create the building blocks of the cage with therapeutic proteins attached to every unit. Yet another important feature of this system is the use of the beneficial characteristics of a virus to deliver molecules that no virus could deliver, such as synthetic drugs, without pathogenic potential. The nanoparticle drug delivery system does not incorporate an attenuated virus, but just a shell of proteins that form regular geometric shapes.

In an embodiment of the present invention, a self-assembling nanoparticle drug delivery system is provided comprising a capsid comprised of viral capsid proteins, a drug captured in the capsid, and a lipid bi-layer enveloping the capsid. In another embodiment of the present invention the viral capsid protein is Hepatitis B Virus (HBV) core protein having the amino acid sequence of SEQ ID NO. 1 or SEQ ID NO. 2.

In another embodiment of the present invention, the viral capsid protein is mutated such that a protease recognition site replaces amino acids 79 and 80 of said HBV core protein. The protease recognition site can be a thrombin recognition site or a factor Xa recognition site.

In another embodiment of the present invention, the HBV C-protein is mutated such that at least one amino acid of SEQ ID NO. 1 or SEQ ID NO. 2 selected from the group consisting of phenylalanine 23, aspartic acid 29, threonine 33, leucine 37, valine 120, valine 124, arginine 127 and tyrosine 132 is changed to a cysteine.

In an embodiment of the present invention, the drug is selected from the group consisting of peptides, proteins, nucleic acids and small molecule synthetic chemical drugs. In another embodiment of the present invention the lipid bi-layer is comprised of phospholipids such as phosphotidyl ethanolamine.

In another embodiment of the present invention, the self-assembling nanoparticle drug delivery system further comprises either or both of cholesterol-tagged polyethylene glycol and cholesterol-tagged protein transduction domains. Suitable protein transduction domains include the Human Immunodeficiency Virus transactivator of transcription or poly-arginine.

In yet another embodiment of the present invention, the self-assembling nanoparticle drug delivery system further comprises an antibody targeting molecule.

In an embodiment of the present invention, a method for constructing a self-assembling nanoparticle drug delivery system is provided comprising mixing a drug with HBV core protein to form a cage solution, encapsulating the drug in the core protein cage by raising the ionic strength of the cage solution, adding phospholipids to the cage solution, adding cholesterol-tagged polyethylene glycol to the cage solution, adding cholesterol-tagged protein transduction domain to the cage solution and purifying the nanoparticles by centrifugation or size exclusion chromatography.

In another embodiment of the present invention, the method for constructing a self-assembling nanoparticle drug delivery system further comprises the step of adding an envelopment guiding protein or peptide after the encapsulating step. In yet another embodiment of the present invention, the envelopment guiding protein is Hepatitis B Virus S-protein or the transmembrane engineered peptide of SEQ ID NO. 5.

In an embodiment of the present invention, the protein transduction domain comprises the Human Immunodeficiency Virus trans-activator of transcription or poly-arginine.

In another embodiment of the present invention, the method for constructing a self-assembling nanoparticle drug delivery system further comprises the step of inserting targeting antibodies into the lipid bi-layer.

In yet another embodiment of the present invention, a method of treating disease with a self-assembling nanoparticle drug delivery system is provided comprising delivering nanoparticles across a mucosal surface.

DETAILED DESCRIPTION OF THE INVENTION

Figure 1:
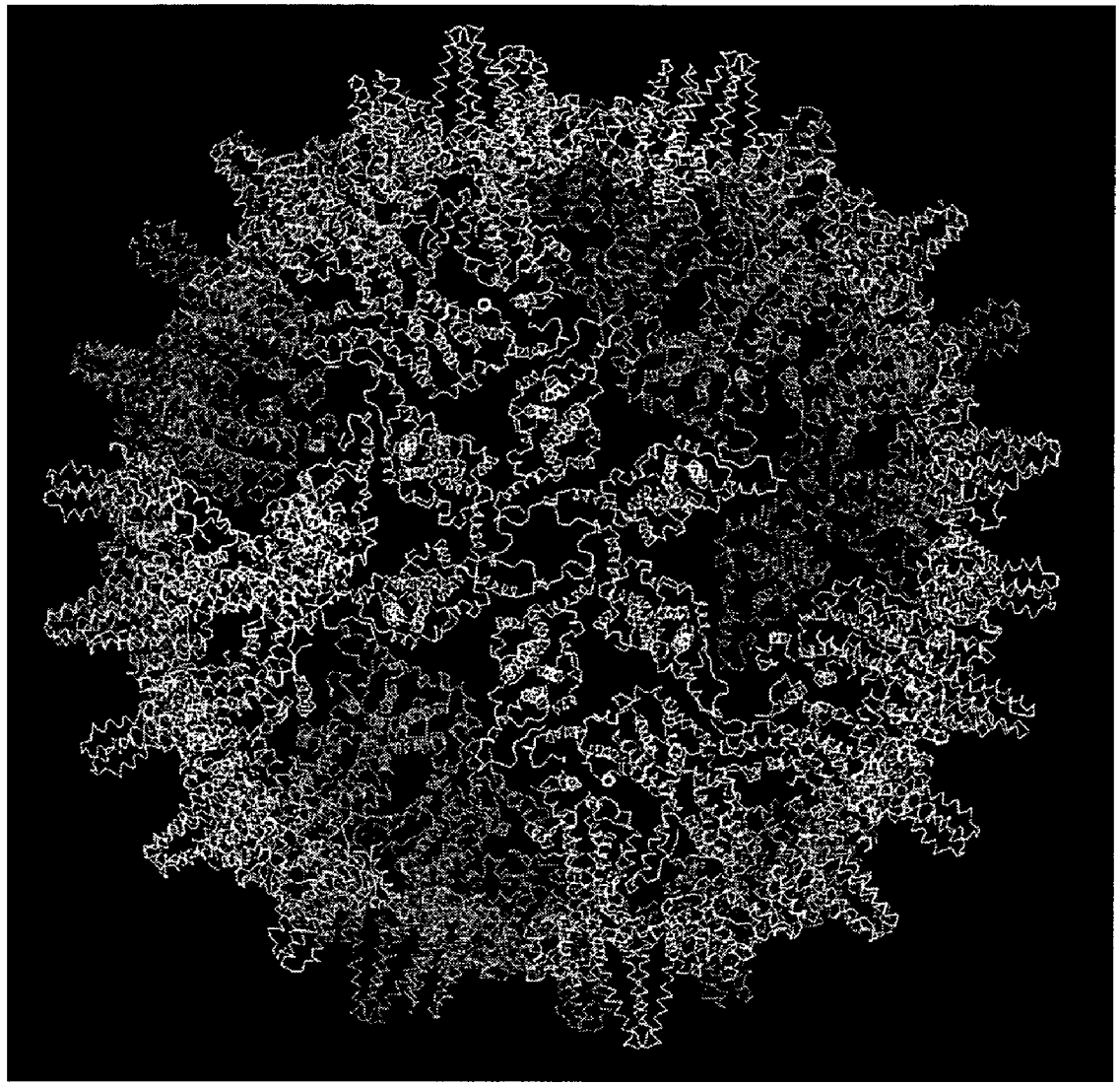
FIG. 1 depicts a computational reconstruction of wild-type Hepatitis B Virus (HBV) capsid reconstructed from electron density maps of the full size HBV dimer from the perspective of looking down at the 6-fold axis.
Figure 2:
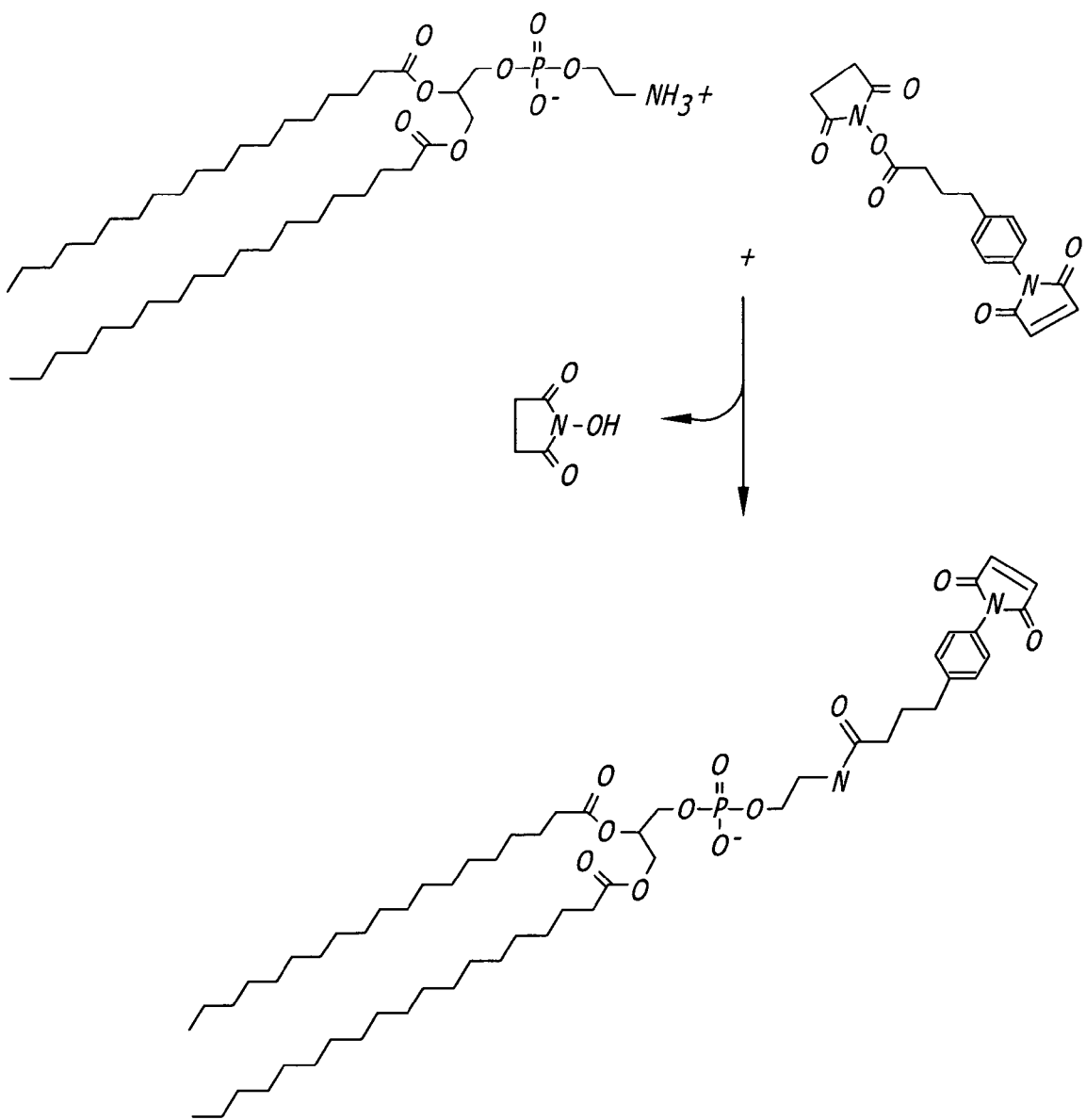
FIG. 2 depicts a flow diagram for phosphatidyl ethanolamine (PE) conjugation to protein cage via a succinimidyl-4-(p-maleimidophenyl)butyrate intermediate according to the teachings of the present invention.
Figure 3:
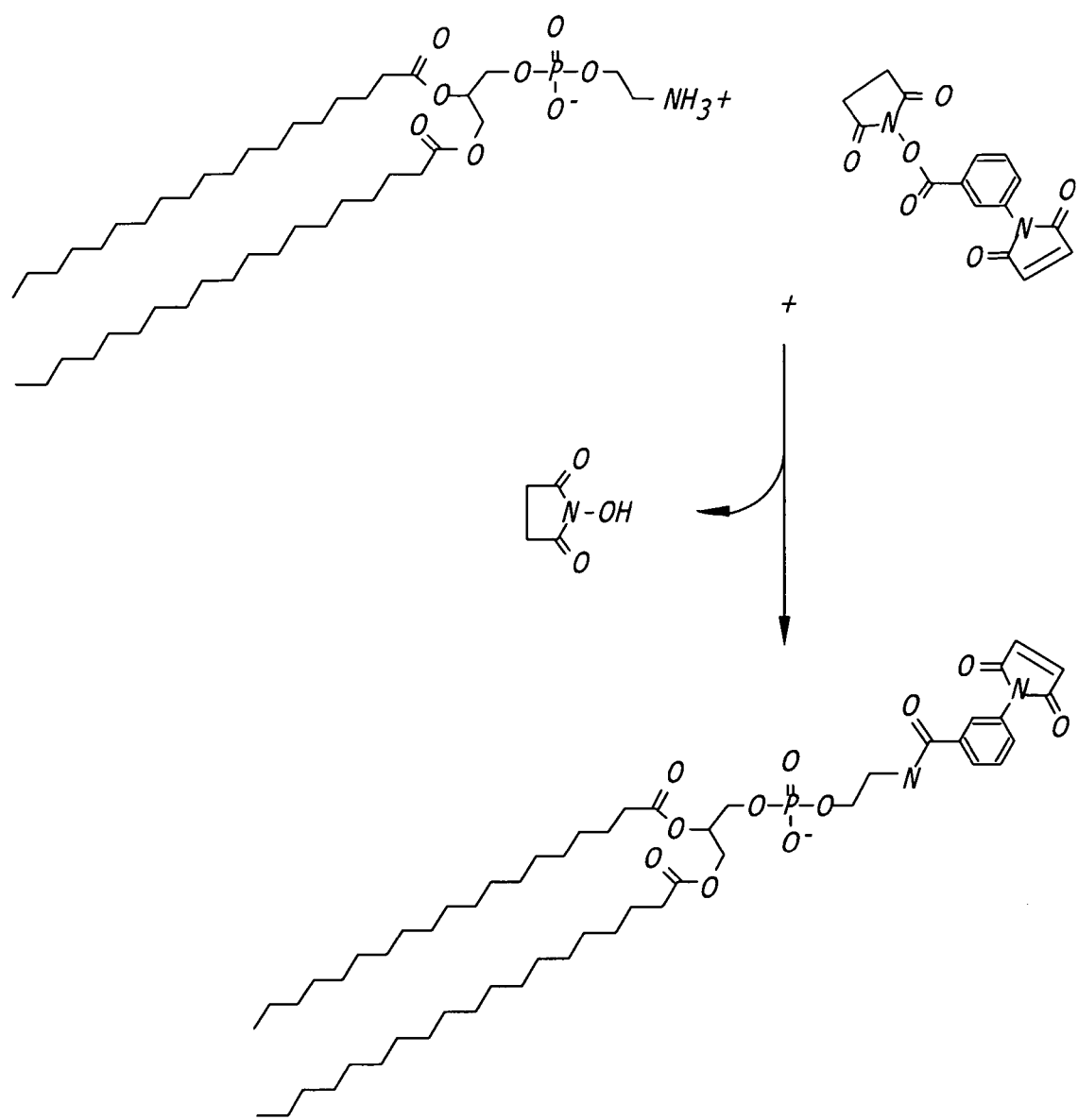
FIG. 3 depicts a flow diagram for PE conjugation to protein cage via m-maleimidobenzoyl-N-hydroxysuccinimide ester intermediate according to the teachings of the present invention.

The present invention provides for a novel nanoparticle drug delivery system that can be administered across mucosal barriers and is able to transport a wide range of molecules including therapeutic proteins into the circulatory system. The nanoparticles of the present invention comprise building blocks re-engineered from natural proteins which self-assemble to form nanocages. During the assembly process, drugs are captured by the specific chemistries of the inward facing surfaces of the cage-forming blocks by simple diffusion/concentration mechanics. The assembled cage has special functionalities to guide the assembly of a surrounding envelope, which is an encapsulating self-assembling double layer of anionic or cationic lipids. Peptides that facilitate membrane transduction will be integrated into the lipid bilayer envelope to endow the system with the ability to pass through cell walls. Polyethylene glycol (PEG) of varying chain lengths can also be anchored into the membrane for the purpose of eluding the immune system and to fend off attacking degradative enzymes. This multilayered delivery system orchestrates a complex arrangement of biomolecules and is entirely self-assembling. The nanoparticle drug delivery system can be administered by any route that includes passage through a mucosal layer such as oral, transdermal, intranasal and buccal routes.

The present invention represents a synthetically enveloped non-viral capsule composed of re-engineered biological molecules and enhanced with synthetic chemical components. Although this design is inspired by the natural behavior of viruses, and uses viral capsid proteins as the building blocks, this system is non-replicating. In addition, all of the proteins used to make the building blocks of the system were all re-engineered to exhibit desired characteristics by altering stabilities and removing or adding disulfide linkages. The building blocks are designed so that once the cage starts to disintegrate, they are degraded quickly so as to limit any potential immune response. A characteristic of this drug delivery system is its ability to create the building blocks of the cage with therapeutic proteins attached to every unit. Yet another important feature of this system is the use of the beneficial characteristics of a virus to deliver molecules that no virus could deliver, such as synthetic drugs, without pathogenic potential. The nanoparticle drug delivery system does not incorporate an attenuated virus, but just the capsid, a shell of proteins that form regular geometric shapes.

The nanoparticle drug delivery system of the present invention can be used to delivery a variety of different types of drugs. In an embodiment of the present invention, an individual nanoparticle of the nanoparticle drug delivery system can contain one or more than one drug. Non-limiting examples of drugs suitable for use with the nanoparticle drug delivery system of the present invention include bioactive agents such as cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antineoplastics, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

An exemplary protein for constructing the nanocage of the nanoparticle drug delivery system of the present invention is Hepatitis B Virus (HBV) core protein (C-protein) (SEQ ID NO. 1), a protein that naturally self-assembles to form the protein capsid of the virus. Different strains of HBV have slight variations in the sequence of C-protein. An example of an alternative HBV C-protein amino acid sequence is disclosed in SEQ ID NO. 2. Core protein was chosen not only because it self-assembles into a capsid, but also because it is the only necessary component to form a complete capsid. Any viral capsid protein which self-assembles into a capsid from a single protein monomer is suitable for use in the nanoparticle drug delivery system of the present invention. Non-limiting examples of self-assembling capsid proteins include human and duck Hepatitis B Virus core protein, Hepatitis C Virus core protein, Human Papilloma Virus type 6 L1 and L2 protein and cowpea chlorotic mottle virus coat protein. The HBV C-protein is 183 amino acids in size with a high concentration of positively charged amino acids at the C-terminus that dangle into the interior of the capsid when assembled. This dangling tail can be engineered so as to specifically interact with molecules of a given characteristic. For example, the natural state of the protein has a cluster of positive charges at the C-terminus that can interact with negatively charged molecules such as DNA or RNA. The C-protein can be engineered so that the C-terminal tail has a cluster of negative charges (Asp or Glu residues) that can interact with positively charged molecules.

SEQ ID NO. 1: HBV C-protein amino acid sequence 1 to 183 (NCBI Protein Database Accession Number BAD86623, the entire disclosure of which is herein incorporated in its entirety):

```
MET ASP ILE ASP PRO TYR LYS GLU PHE GLY ALA SER VAL GLU LEU  (15)

LEU SER PHE LEU PRO SER ASP PHE PHE PRO SER ILE ARG ASP LEU  (30)

LEU ASP THR ALA SER ALA LEU TYR ARG GLU ALA LEU GUI SER PRO  (45)

GLU HIS CYS SER PRO HIS HIS THR ALA LEU ARG GLN ALA ILE LEU  (60)

CYS TRP GLY GLU LEU MET ASN LEU ALA THR TRP VAL GLY SER ASN  (75)

LEU GLU ASP PRO ALA SER ARG GLU LEU VAL VAL SER TYR VAL ASN  (90)

VAL ASN MET GLY LEU LYS ILE ARG GLN LEU LEU TRP PHE HIS ILE  (105)

SER CYS LEU THR PHE GLY ARG GLU THR VAL LEU GLU TYR LEU VAL  (120)

SER PHE GLY VAL TRP ILE ARG THR PRO PRO ALA TYR ARG PRO PRO  (135)

ASN ALA PRO ILE LEU SER THR LEU PRO GLU THR THR VAL VAL ARG  (150)

ARG ARG GLY ARG SER PRO ARG ARG ARG THR PRO SER PRO ARG ARG  (165)
```

-continued
```
ARG ARG SER GLN SER PRO ARG ARG ARG ARG SER GLN SER ARG GLU   (180)

SER GLN CYS                                                   (183)
```

SEQ ID NO. 2: HBV C-protein alternative amino acid sequence 1 to 183 (NCBI Protein Database Accession Number AY741795, the entire disclosure of which is herein incorporated in its entirety):

```
MET ASP ILE ASP PRO TYR LYS GLU PHE GLY ALA THR VAL GLU LEU   (15)

LEU SER PHE LEU PRO SER ASP PHE PHE PRO SER VAL ARG ASP LEU   (30)

LEU ASP THR ALA SER ALA LEU TYR ARG GLU ALA LEU GLU SER PRO   (45)

GLU HIS CYS SER PRO HIS HIS THR ALA LEU ARG GLN ALA ILE LEU   (60)

CYS TRP GLY GLU LEU MET THR LEU ALA THR TRP VAL GLY ASN ASN   (75)

LEU GLU ASP PRO ALA SER ARG ASP LEU VAL VAL ASN TYR VAL ASN   (90)

THR ASN MET GLY LEU LYS ILE ARG GLN LEU LEU TRP PHE HIS ILE   (105)

SER CYS LEU THR PHE GLY ARG GLU THR VAL LEU GLU TYR LEU VAL   (120)

SER PHE GLY VAL TRP ILE ARG THR PRO PRO ALA TYR ARG PRO PRO   (135)

ASN ALA PRO ILE LEU SER THR LEU PRO GLU THR THR VAL VAL ARG   (150)

ARG ARG GLY ARG SER PRO ARG ARG ARG THR PRO SER PRO ARG ARG   (165)

ARG ARG SER GLN SER PRO ARG ARG ARG ARG SER GLN SER ARG GLU   (180)

SER GLN CYS                                                   (183)
```

HBV C-protein assembles to form an icosahedral viral capsid. Viruses are macromolecular complexes, composed of a nucleic acid genome enclosed in a protein coat (or capsid) and sometimes a lipid membrane. Viral genomes are usually very small and may be composed of as few as three genes. The virus must, therefore, be extremely efficient in its use of genetic material and consequently the capsid (which protects the viral genome in the harsh extracellular environment) must assemble from a small number of gene products. Asymmetric viral protein monomers are arranged such that they occupy identical bonding environments. Spherical viruses, such as HBV, assemble as icosahedra, which are 20-sided polyhedra composed of 60 asymmetric unites arranged as equilateral triangles. The viral icosahedral capsids assemble from one protein species in $60_n$ subunits. These icosahedra are described by their triangulation number (T) where there are 60T subunits.

The full length HBV C-protein forms particles (T=4) with a diameter of approximately 36 nanometers (Crowther R A et al., Three-dimensional structure of hepatitis B virus core particles determined by electron cryomicroscopy, Cell 77:943-50, 1994). Inside this particle, the final 40 amino acids of the C-protein are thought to interact with the genomic DNA of the virus. Core protein constructs lacking this putative DNA-binding region also form icosahedral capsids, but with a triangulation number of three (T=3). Interactions between C-protein monomers in these two types of capsids are thought to be similar.

In HBV capsids, C-protein monomers form dimers that associate tightly via a "spike." The spike is a central four alpha-helical bundle (Bottcher B et al., Determination of the fold of the C-protein of hepatitis B virus by electron cryomicroscopy, Nature 386:88-91, 1997) with a 2-fold axis of symmetry. The icosahedral viral capsid consists of 120 C-protein dimers assembled around 5-fold and 6-fold axes in a rough head-to-tail type interaction. In the mature virus, the tips of the central spikes of the 120 dimers are oriented close to the surface of the particle where it is coated by a plasma membrane envelope. A computational reconstruction of wild-type HBV capsid reconstructed from electron density maps of the full size HBV dimmer with the perspective of looking down at the 6-fold axis is depicted in FIG. 1. This figure is representative of what a naked nanocage looks like prior to envelopment.

In vitro assembly of empty HBV capsids using the dimeric 149 residue assembly domain of the C-protein (amino acids 1-149) can be induced by high NaCl concentration. In HBV, subunit dimers are stable in solution. Assembly of HBV conforms to thermodynamic and kinetic predictions of the simplest case assembly models. Assembly reactions appear to contain only dimer and capsid and show a predicted steep concentration dependence. This assembly demonstrates a remarkably weak association constant, yet capsids assemble because subunits are multivalent. Capsids are even more stable than the association constant would predict because there is a steep energy barrier which inhibits disassociation (Zlotnick A, Are weak protein-protein interactions the general rule of capsid assembly? Virology 315:269-274, 2003).

In an embodiment of the present invention, mutations are engineered into the HBV C-protein in the spike area of the dimer or the interface between dimers. Mutations in the spike are used to introduce functional groups at the surface of the capsid in order to promote envelopment by a plasma membrane. In another embodiment of the present invention, a "protease recognition loop" is engineered in the spike which facilitates the breakdown of the entire capsid once it reaches the bloodstream. Mutations in the interface will stabilize the capsid and "tune" the lifetime of the capsid prior to disassembly.

In one embodiment of the present invention, in order to attach functional groups, either of the amino acids cysteine or lysine are placed at the tip of the spike in such a way as they protrude away from the capsid surface toward the plasma membrane envelope. In a non-limiting example, three positions (77, glutamic acid to cysteine; 78, aspartic acid to cysteine; and 80, alanine to cysteine) have been identified for the introduction of these amino acids which are functionalized at a later stage. It is within the scope of the present invention to introduce cysteine mutations at other locations in the C-protein. The choice of lysine or cysteine at each position is dependent of the orientation and geometry of each amino acid as judged from the crystal structure of the HBV capsid (Wynne S A et al., The crystal structure of the human hepatitis B virus capsid, Molecular Cell 3:771-80, 1999). Because of the 2-fold symmetry of the 4-helical bundle, an introduction of one reactive amino acid at each single position gives a total of two bioconjugated molecules per spike.

In another embodiment of the present invention, pairs of cysteines are introduced at the interface between monomers in such a way that they will promote and strengthen the assembly. In a non-limiting example, the first cysteine (e.g. amino acid 23) is introduced in the first position in order to disulfide bond with the second position (amino acid 132 in this case) in a neighboring molecule. Similarly, the second position also participates in a disulfide bond, allowing the dimer to participate in four disulfide bridges and a total of 180 stabilizing covalent interactions. In one embodiment of the present invention, four different types of disulfide bonds, according to their effectiveness in stabilizing the assembly and the desired strength of the assembly, are created:

Mutation 1: Phenylalanine 23 to cysteine; tyrosine 132 to cysteine

Mutation 2: Aspartic acid 29 to cysteine; arginine 127 to cysteine

Mutation 3: Threonine 33 to cysteine; valine 124 to cysteine

Mutation 4: Leucine 37 to cysteine; valine 120 to cysteine

Once an HBV C-protein-derived nanoparticle has traveled into the bloodstream, it is necessary for it to disassemble into its component monomers so that it can release its therapeutic cargo. To expedite this process, in an embodiment of the present invention, the spike-forming region of the monomer is engineered to contain a blood protease-recognition sequence. The protease recognizes and cleaves this loop and thereby promotes disassembly. The two most commonly used blood proteases for this type of application are thrombin and factor Xa (Jenny R J et al., A critical review of the methods for cleavage of fusion proteins with thrombin and factor Xa, Protein Expr Purif. 31:1-11, 2003, which is herein incorporated by reference for all it contains regarding cleavage of proteins by thrombin and factor Xa). The specificities of these two proteases are well-known (Stevens R C, Drug Discovery World, 4:35-48, 2003) and can be readily incorporated into the internal loop of the C-protein. Thrombin is probably the best choice for specificity of these sites as there is known to be a constant, resting level of thrombin in the blood (Fernandez J A et al., Activated protein C correlates inversely with thrombin levels in resting healthy individuals, Am J Hematol. 56:29-31, 1997). Sequences identified as SEQ ID NO. 3 and SEQ ID NO. 4 have an extended loop and a recognition sequence for either thrombin (SEQ ID NO. 3) or factor Xa (SEQ ID NO. 4) inserted into the spike region of the HBV C-protein (replacing amino acids 79 and 80 with the 12 amino insertion loop of SEQ ID NO. 3 or SEQ ID NO. 4).

SEQ ID NO. 3: 12 amino acid insertion loop encoding a thrombin site.

GLY PRO GLY ALA PRO GLY LEU VAL PRO ARG GLY SER

SEQ ID NO.4: 12 amino acid insertion loop encoding a Factor Xa site.

GLY PRO ALA SER GLY PRO GLY ILE GLU GLY ARG ALA

The recombinant C-protein can expressed and purified using common molecular biology and biochemistry techniques. In another embodiment of the present invention, recombinant expression vectors may be used which are engineered to carry the HBV C-protein gene into a host cell to provide for expression of the HBV C-protein. Such vectors may be introduced into a host cell by transfection means including, but not limited to, heat shock, calcium phosphate, DEAE-dextran, electroporation or liposome-mediated transfer. Recombinant expression vectors include, but are not limited to, *Escherichia coli* based expression vectors such as BL21 (DE3) or pLysS, COS cell-based expression vectors such as CDM8 or pDC201, or CHO cell-based expression vectors such as pED vectors. The C-protein gene coding region may be linked to one of any number of promoters in an expression vector that can be activated in the chosen cell line. Additionally this cassette (capsid gene and promoter) is carried by a vector that contains a selectable marker such that cells receiving the vector may be identified.

Promoters to express the capsid proteins within a cell line may be drawn from those that are functionally active within the host cell. They may include, but are not limited to, the T7 promoter, the CMV promoter, the SV40 early promoter, the herpes TK promoter, and others well known in recombinant DNA technology. Inducible promoters may be used, including but not limited to, the metallothionine promoter (MT), the mouse mammary tumor virus promoter (MMTV), and others known to those skilled in the art.

Selectable markers and their attendant selection agents can be drawn from the group including, but not limited to, ampicillin, aminoglycoside phosphotransferase/G418, hygromycin-B phosphotransferase/hygromycin-B, and amplifiable selection markers such as dihydrofolate reductase/methotrexate and others known to skilled practitioners.

Other embodiments of the present invention include the use of eukaryotic, prokaryotic, insect, plant, and yeast expression systems to express the HBV C-protein. In order to express capsid proteins the nucleotide sequence coding for the protein is inserted into an appropriate expression vector, i.e., a vector which contains the necessary elements for the transcription and translation of the inserted coding sequences. Methods which are well known to those skilled in the art can be used to construct expression vectors containing the protein coding sequences operatively associated with appropriate transcriptional/translational control signals. These methods include in vitro recombinant DNA techniques, synthetic techniques, and in vivo recombination/genetic recombination. See, for example, the techniques and vectors described in Maniatis, et al., 1989, Molecular Cloning, A Laboratory Manual, Cold Spring Harbor Laboratory, N.Y. and Ausubel et al., 1989, Current Protocols in Molecular Biology, Greene Publishing Associates & Wiley Interscience, N.Y.

A variety of eukaryotic, prokaryotic, insect, plant and yeast expression vector systems (i.e.—vectors which contain the necessary elements for directing the replication, transcription, and translation of capsid protein coding sequences) may be utilized equally well by those skilled in the art, to express capsid protein coding sequences. These include but are not limited to microorganisms such as bacteria transformed with recombinant bacteriophage DNA, plasmid DNA or cosmid DNA expression vectors containing the capsid protein coding sequences; yeast transformed with recombinant yeast expression vectors containing the capsid protein coding sequences; insect cell systems infected with recombinant virus expression vectors (e.g., baculovirus) containing the capsid protein coding sequences; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the capsid protein coding sequences.

In an embodiment of the present invention, the full length HBV C-protein gene was cloned into a pET-11a expression vector and expressed in *Escherichia coli* DE3 cells as described in Example 1.

Expressed C-protein in solution forms a dimer that is naturally stabilized by salt bridges, hydrophobic interactions, and covalent inter- and intra-molecular disulfide bonds. In an embodiment of the present invention, the intra-molecular bonds are engineered so that C-protein stability can be tuned to a desired level. In addition, inter-molecular disulfide bonds are engineered so as to affect the stability of the cage. Specific salt bridges between dimers that help form the capsid can be mutated to cysteines so that disulfide bonds form and stabilize the capsid structure. All modifications of C-protein are based on an extensive analysis of the capsid crystal structure and energy minimization models performed on electron density maps derived from structural data.

In another embodiment of the present invention, C-protein is engineered so as to contain protease recognition sites at hinge and loop regions. The immunodominant spike of the C-protein can accommodate insertions of at least 46 residues and still be able to form capsids. Recognition sites for proteases including, but not limited to, thrombin and Factor Xa, are inserted at this location. These recognition sites add the benefit of quick degradation of the building blocks after the entire system has started to fall apart as a time-release method of distributing the encapsulated bioactive agents. This will minimize the possibility of an immune response to the presence of "naked" C-protein in the blood stream.

In another embodiment of the present invention, the C-terminal tail of the C-protein is replaced with a therapeutic protein (drug). For the purposes of this disclosure, the term protein refers to both proteins and peptides. The C-terminus is engineered at the genetic level so as to create a chimeric building block of C-protein and the therapeutic protein (fusion protein). The therapeutic protein is linked to the C-protein by a tether of amino acids that codes for a specific protease recognition site. This allows the therapeutic protein to be freed after the cage begins to fall apart. In another embodiment of the present invention, the therapeutic protein is linked to the C-protein though a disulfide bridge between cysteine residues in the C-terminal tail of C-protein and in the protein drug. The cysteine residues can be those already present in the proteins or they can be engineered at the desired location of each protein.

In another embodiment of the present invention, cysteine residues are engineered in the outer spike region of the capsid so that a modified Hepatitis B Virus S-protein can be covalently linked. The S-protein functions to guide the lipid bi-layer formation of the envelope. In an embodiment of the present invention, the S-proteins are modified to have cysteines as well to complement the disulfide bridge formation between C-protein monomers.

In an embodiment of the present invention, the S-protein can be replaced by a peptide with similar characteristics to guide envelopment of the cage, such as a transmembrane engineered peptide. An exemplary transmembrane engineered peptide suitable for this purpose would have a flexible region that ends with a cysteine so as to form disulfide bridges with the cage. The opposite end of the peptide is comprised primarily of hydrophobic residues. A non-limiting example of such a transmembrane engineered peptide is disclosed in SEQ ID NO. 5. The hydrophobic region of this peptide associates with the hydrophobic lipid bi-layer region, thus acting to guide the formation of a tight vesicle around the cage. These guiding peptides are added to the reaction mix after the formation of the cage and disulfide link to the C-protein.

SEQ ID NO. 5: HBV S-protein transmembrane engineered peptide:

```
CYS ALA ARG GLY ALA ARG GLY ALA ARG GLY ALA ARG GLY ILE LEU      (15)

GLY VAL PHE ILE LEU LEU TYR MET                                  (23)
```

In yet another embodiment of the present invention, in an alternative to the S-protein or equivalent transmembrane engineered peptides described above, phospholipids can be directly linked to the C-protein core to guide envelopment. At the apex of the spike region of core protein a cysteine residue is mutated as disclosed above and at this site fatty acids, including, but not limited to, modified phosphatidyl serine, are covalently attached. These fatty acids act as a guide for other phospholipids and cholesterols to form a bilayer around the nanocage. This replaces the necessity of S-protein or the previously discussed transmembrane engineered peptide. Also with the addition of these covalently attached phospholipids to the spike region (also known as the immunodominant spike), immune responses may be repressed.

In one embodiment of the invention, the lipid bi-layer in this method comprises phospholipids. In another embodiment of the invention, the envelope-forming components further includes cholesterol, including a PEG-phospholipid. In certain embodiments of the invention, the PEG-phospholipid comprises poly(ethylene glycol)-derivatized distearoylphosphatidylethanolamine (PEG-DSPE) and/or poly(ethylene glycol)-derivatized ceramides (PEG-CER).

Phospholipids suitable for forming the nanoparticle envelope include, but are not limited to, hydrogenated soy phosphatidylcholine (HSPC), egg phosphatidylcholine (EPC), phosphatidyl ethanolamine (PE), phosphatidyl glycerol (PG), phosphatidyl insitol (PI), monosialogangolioside, spingomyelin (SPM), distearoylphosphatidylcholine (DSPC), dimyristoylphosphatidylcholine (DMPC), or dimyristoylphosphatidylglycerol (DMPG).

In an embodiment of the present invention, the nanoparticle envelope is modified to allow the particles to evade the immune system and to enter the target cells. Cholesterol-tagged polyethylene glycol (PEG) and/or protein transduction domains (PTD) are added to the mixture. Non-limiting examples of suitable PTDs are the Human Immunodeficiency Virus (HIV) transactivator of transcription (Tat) peptide or poly-arginine (poly-Arg). First cholesterol-tagged PEG is anchored into the lipid bi-layer and then cholesterol tagged PTDs are anchored into the lipid bilayer. The modified PEG and PTDs are added to enveloped nanocages and insert into the envelope surface in a concentration dependent manner.

In a further embodiment of the present invention, targeting agents are incorporated into the lipid envelope to direct the nanoparticle to a tissue or cell target. An exemplary embodiment of a targeting agent is an antibody. Antibodies are comprised of two heavy and two light chains associated through disulfide bonds into two heavy chain-light chain complexes associated through exposed disulfide bonds in the heavy chain. In the presence of weak reducing agents such as β-mercaptoethanol, the heavy chains are dissociated leaving the heavy chain-light chain associations intact. Exposed sulfhydryl groups on the heavy chain can then be used to link the antibody to the free sulfate groups on the lipid envelope. The resultant nanoparticles are comprised of drug encapsulated in a protein cages which is enveloped in a lipid-targeting antibody coating.

In another embodiment of the present invention, the reduced antibody heavy chain-light chain complex above can be attached directly to the naked protein cage. As discussed above, the protein building blocks can be engineered to incorporate cysteine residues with reactive sulfhydryl groups which then can be linked with the partially disassociated antibody chains. This configuration of nanoparticles results in drug encapsulated in a protein cage tagged with antibody targeting molecules.

Antibody suitable for use as targeting agents in the nanoparticle drug delivery system of the present invention include antibodies directed to cell surface antigens which cause the antibody-nanoparticle complex to be internalized, either directly or indirectly. Specific non-limiting examples of suitable antibodies include antibodies to CD33 and CD22. CD33 and CD22 are over-expressed and dimerized on lymphomas and binding to these antigens caused endocytosis and thereby internalization of the antibody-nanoparticle complex.

In an embodiment of the nanoparticle drug delivery system of the present invention, the nanoparticle can comprise a drug encapsulated in a viral capsid nanocage. In another embodiment of the present invention, the nanoparticle can comprise a drug encapsulated in a viral capsid nanocage further including targeting antibodies. In yet another embodiment of the present invention, the nanoparticle can comprise a drug encapsulated in a viral capsid nanocage further including PEG molecules.

A therapeutic agent encapsulated in the nanoparticle drug delivery system of the present invention can be administered by any conventional route. These include, but are not limited to the systemic routes, e.g. subcutaneous, intradermal, intramuscular or intravenous route, and mucosal routes, e.g. oral, nasal, pulmonary or anogenital route. When the treatment of solid tumors is involved, the intratumor route may also be used. When the treatment of genetic diseases is involved, the choice of the route of administration will essentially depend on the nature of the disease; for example, there may be advantageously mentioned the pulmonary route in the case of cystic fibrosis (the nanoparticles being formulated in aerosol form) or the intravenous route in the case of hemophilia.

The nanoparticles of the nanoparticle drug delivery system of the present invention are administered in a biocompatible aqueous solution. This solution can be comprised of, but not limited to, saline or water and optionally contains pharmaceutical excipients including, but not limited to, buffers, stabilizing molecules, preservatives, sugars, amino acids, proteins, carbohydrates and vitamins.

For increasing the long-term storage stability, the nanoparticles of the nanoparticle drug delivery system of the present invention may be frozen and lyophilized in the presence of one or more protective agents such as sucrose, mannitol, trehalose or the like. Upon rehydration of the lyophilized nanoparticles, the suspension retains essentially all drug previously encapsulated and retains the same particle size. Rehydration is accomplished by simply adding purified or sterile water or 0.9% sodium chloride injection or 5% dextrose solution followed by gentle swirling of the suspension. The potency of drug encapsulated in the nanoparticle is not lost after lyophilization and reconstitution.

The administration of nanoparticles may be carried out at a single dose or at a dose repeated once or several times after a certain time interval. The appropriate dosage varies according to various parameters, for example the individual treated or the mode of administration. Appropriate doses will be established by persons skilled in the art of pharmaceutical dosing such as physicians.

Figure 5:
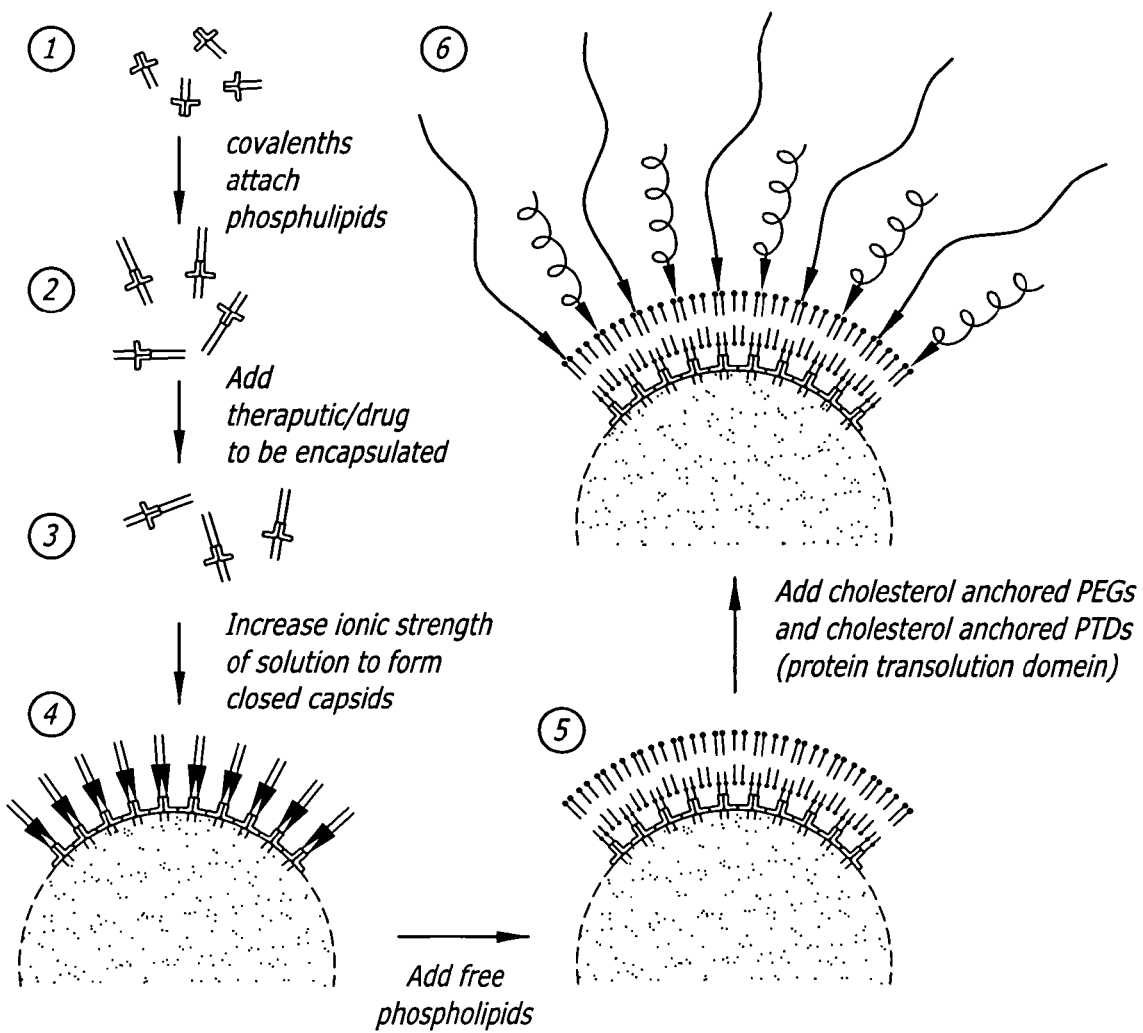
FIG. 5 depicts a flow diagram of the construction of a self-assembling nanoparticle drug delivery system according to the teachings of the present invention.

An exemplary embodiment of the process of assembling the nanoparticle drug delivery system of the present invention is depicted in FIG. 5, the steps of which are summarize below:

1. Engineered C-protein mixed with the drug of choice;
2. ionic strength of solution raised with the addition of NaCl to form cages, encapsulating drug inside;
3. engineered S-protein or engineered peptide added to the cages;
4. sonicated phospholipids solution added to the mixture;
5. cholesterol-tagged polyethylene glycol is added to the mixture;
6. cholesterol-tagged protein transduction domains are added to the mixture; and
7. purification of the system by centrifugation or size exclusion chromatography.

More specifically, the drug is incorporated into the nanoparticle drug delivery system of the present invention during the assembly of the cage. Core protein in a mildly buffered solution is mixed with a drug. As will be well known to those skilled in the art, a buffer system compatible with both C-protein and the drug is used. Examples of suitable buffers include, but are not limited to, phosphate, citrate and Tris buffers as well as other buffers well known to those skilled in the art. In an exemplary embodiment of present invention, protein drugs are encapsulated in protein nanocages. Nanocages comprised of HBV C-protein can be packed with up to 1200 copies of a 10 kDa protein or an equivalent amount of at least one of a protein, peptide, nucleic acid or small molecule synthetic chemical entity. Therapeutic protein:C-protein complexes form in just a few seconds after mixing as dictated by the general physics of molecular diffusion and coulombic attraction. After 5-10 minutes, the ionic strength of the solution is raised by the addition of NaCl to a final concentration of 0.6 M, triggering the self-assembly reaction of the capsid. After incubating the mixture for one hour the presence of fully formed capsids is verified using standard biochemical analyses. Next the cage is mixed with either re-engineered S-protein or with a transmembrane engineered peptide as disclosed above. These additions will covalently link to a complementary cysteine on the surface of the cage at the spike of each building block.

In another embodiment of the present invention, phospholipids are incorporated into the C-protein matrix. The most stable association involves covalently combining a phospholipid to a functional group found on the side chains of specific amino acids within the C-protein. In the two similar protocols presented in Examples 2 and 3, heterobifunctional cross-linking molecules are utilized in order to provide a wide template for which many different functional groups found on different amino acids can be utilized, with the goal of optimizing distance constraints, solvent interactions, combinations of amino acid residue functional groups and phospholipids, and simplicity of synthesis. Examples 2 and 3 depict the addition of sulfhydryl functional groups to the C-protein. Through these functional groups, phospholipid molecules can then be anchored which guide the envelopment process. In an embodiment of the present invention, suitable ratios of protein:lipid for the envelopment process range from approximately 1:1 protein:lipid (w:w) to approximately 1:20 protein:lipid (w:w).

The use of heterobifunctional cross-linking molecules allows the possibility of engineering different functional groups at appropriate anchor points along the C-protein matrix while using the same phospholipid precursors, if necessary. For example, sulfhydryl functional groups are also involved in stabilizing the intermolecular interactions between core proteins that will stabilize the core cage. If utilizing the same functional group for anchoring phospholipids prevents the sulfhydryl functional groups from forming inter-molecular bonds and therefore negatively impacts the stability of the core protein shell, then other functional groups including, but not limited to, hydroxyl and amine groups, can be engineered into the protein at locations where phospholipid anchoring is specifically designed. This merely requires re-engineering the core proteins at a single location, and the use of an alternative, commercially-available heterobifunctional cross-linking molecule.

The envelope layer of the nanoparticle of the present invention is a cationic or anionic lipid bi-layer. In an embodiment of the present invention, a homogeneous mixture of various ratios of lipids (predominately phospholipids) and cholesterol is made by adding dried components to a solution of chloroform: methanol (2:1 by volume). For example, and not intended as a limitation, 100 mg of phosphatidyl choline, 40 mg of cholesterol, and 10 mg of phosphatidyl glycerol are added to 5 mL of chloroform/methanol solution. This mixture is gently shaken to thoroughly mix all components. Next the mixture is dried down so as to remove all organic solvents. This dried mixture is then introduced to a few milliliters of aqueous solution (buffered $H_2O$) and mechanically dispersed by sonication. This solution is quickly added to a suspension of fully assembled nanocages containing captured drug payloads. The nanocages will already have been covalently modified with either envelopment enhancing peptides (engineered or S-protein) or with phospholipids. After a brief incubation with gentle mixing, enveloped cages are separated and purified using simple centrifugation and size exclusion chromatography.

EXAMPLE 1

Core Protein Expression and Purification

A pET-11a vector containing the full-length HBV C-protein gene, is transformed into *E. coli* DE3 cells and grown at 37° C. in LB media, fortified with 2-4% glucose, trace elements and 200 ug/mL carbenicillin. Protein expression is induced by the addition of 2 mM IPTG (isopropyl-beta-D-thiogalactopyranoside). Cells are harvested by pelleting after three hours of induction. SDS-PAGE is used to assess expression of C-protein.

Core protein is purified from *E. coli* by resuspending in a solution of 50 mM Tris-HCl, pH 7.4, 1 mM EDTA, 5 mM DTT, 1 mM AEBSF, 0.1 mg/mL DNase1 and 0.1 mg/mL RNase. Cells are then lysed by passage through a French pressure cell. The suspension is centrifuged at 26000×G for one hour. The pellet is discarded and solid sucrose added to the supernatant to a final concentration of 0.15 M and centrifuged at 10000×G for one hour. The pellet is discarded and solid $(NH_4)_2SO_4$ is then added to a final concentration of 40% saturation, stirred for one hour and then centrifuged for one hour at 26000×G. The pellet is resuspended in a solution of 100 mM Tris-HCl at pH 7.5, 100 mM NaCl, 50 mM sucrose and 2 mM DTT (Buffer A) and loaded onto a Sepharose CL-4B (Pharmacia Biotech, Piscataway, N.J.) column (5 cm diameter×95 cm) equilibrated with Buffer A. and the column eluted at 2 mL/minute. Using this purification scheme, HBV viral capsids are separated from large aggregates and from soluble proteins of lower molecular weight. The fractions are pooled according to chromatographic profile and SDS-PAGE analysis and the solution concentrated by ultrafiltration using Diaflo YM 100 ultrafitration membrane (Amicon, Beverly, Mass.) to about 10 mg/mL. Concentrated C-protein is dialyzed against 50 mM Tris-HCl, pH 7.5 and 0.15 M sucrose. The solution is then adjusted to pH 9.5 with 10N NaOH and urea added to a final concentration of 3.5 M. The solution is then filtered using a Millex-HA 0.45 um pore size filter unit (Millipore, Bedford, Mass.) and applied to a column (6.0 cm diameter×60 cm) of Superdex 75 (Pharmacia Biotech, Piscataway, N.J.) equilibrated with 100 mM sodium bicarbonate, pH 9.5, containing 2 mM DTT. The column is eluted at 5 mL/minute. The fractions containing dimeric protein as assessed by SDS-PAGE are pooled. These procedures will be used for the expression and purification of all core protein mutants. Alternately, the expression of this protein can be done in yeast cells according to methods well known to persons skilled in the art.

EXAMPLE 2

Protocol for Phospholipid Conjugation via SMPB Intermediate (FIG. 2)

1. Dissolve 100 micromoles of phosphatidyl ethanolamine (PE) in 5 mL of argon-purged, anhydrous methanol containing 100 micromoles of triethylamine (TEA). Maintain the solution under an argon or nitrogen atmosphere. The reaction may also be done in dry chloroform.

2. Add 50 mg of SMPB (succinimidyl-4-(p-maleimidophenyl)butyrate, Pierce) to the PE solution. Mix well to dissolve.

3. React for 2 hours at room temperature, while maintaining the solution under an argon or nitrogen atmosphere.

4. Remove the methanol from the reaction solution by rotary evaporation and redissolve the solids in chloroform (5 mL).

5. Extract the water-soluble reaction by-products from the chloroform with an equal volume of 1% NaCl. Extract twice.

6. Purify the MPB-PE derivative by chromatography on a column of silicic acid (Martin F J et al., Immunospecific targeting of liposomes to cells: A novel and efficient method for covalent attachment of Fab' fragments via disulfide bonds. Biochemistry, 1981; 20:4229-38).

7. Remove the chloroform from the MBP-PE by rotary evaporation. Store the derivative at −20 C under a nitrogen atmosphere until use.

EXAMPLE 3

Protocol for Phospholipid Conjugation via MBS Intermediate (FIG. 3)

1. Dissolve 40 mg of PE in a mixture of 16 mL dry chloroform and 2 mL dry methanol containing 20 mg triethylamine, maintain under nitrogen.

2. Add 20 mg of m-maleimidobenzoyl-N-hydroxysuccinimide ester (MBS) to the lipid solution and mix to dissolve.
3. React for 24 hours at room temperature under nitrogen.
4. Wash the organic phase three times with PBS, pH 7.3, to extract excess cross-linker and reaction by-products.
5. Remove the organic solvents by rotary evaporation under vacuum.

EXAMPLE 4

Figure 4:
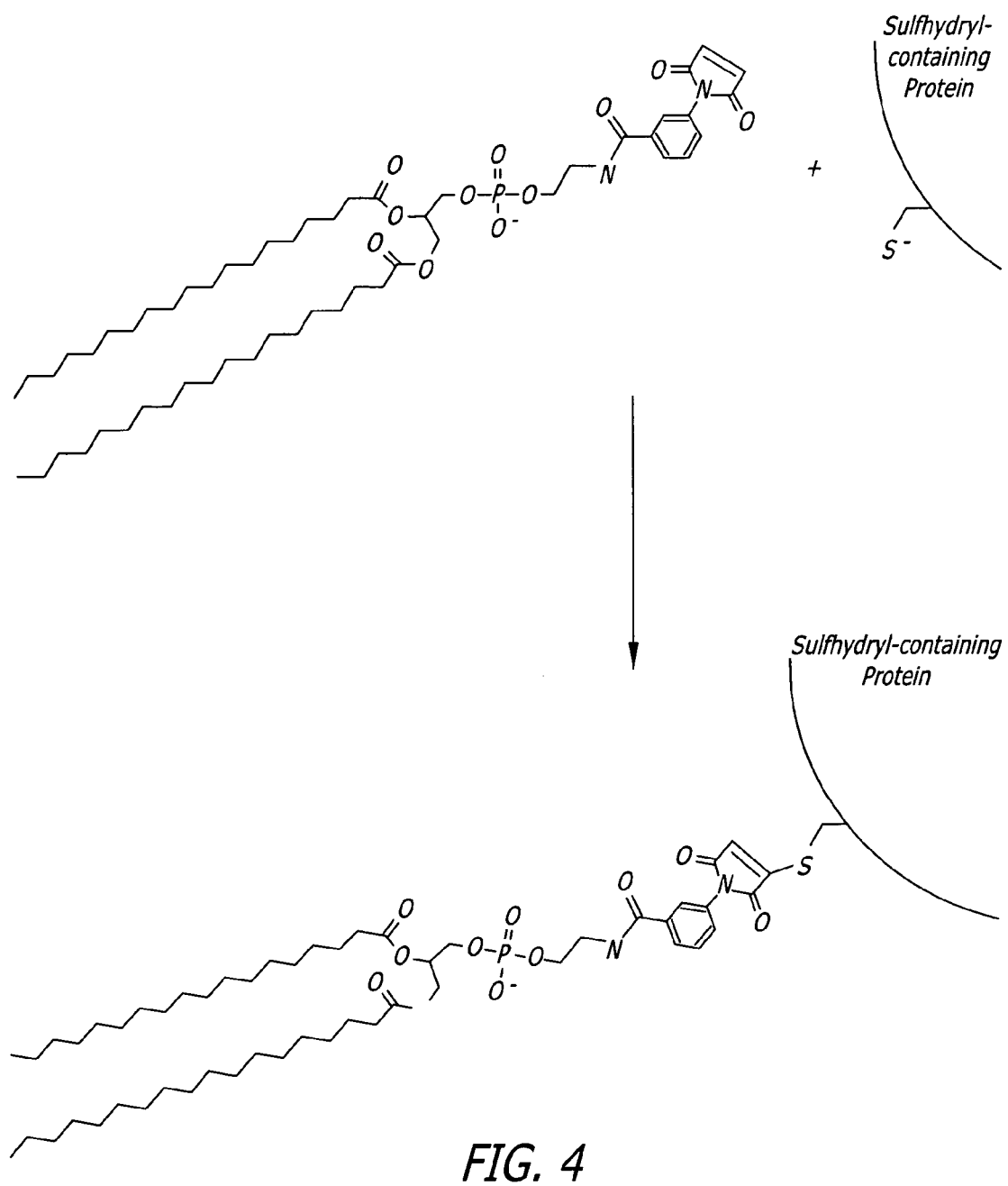
FIG. 4 depicts a flow diagram for conjugating maleimide-containing intermediates to sulfhydryl-containing proteins according to the teachings of the present invention.

Protocol for Conjugating Maleimide-Containing Intermediates (MCI) to Sulfhydryl-Containing Proteins (SCP) (FIG. 4)

1. Dissolve the SCP in TRIS*HCl buffer (pH=8.0, 100 millimolar) to obtain a concentration of 1 millimolar). Purge under a nitrogen or argon atmosphere for 20 minutes.
2. Dissolve the MCI in the same buffer as above, also purge under a nitrogen or argon atmosphere for 20 minutes, to obtain a 10-fold molar excess.
3. Combine the two solutions, and continue purging the solution under a nitrogen or argon atmosphere for an additional 20 minutes.
4. Allow the reaction to proceed for 6 hours, at room temperature.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A self-assembling nanoparticle drug delivery system comprising:
   a capsid comprised of non-replicating viral capsid protein, wherein said viral capsid protein is a modified Hepatitis B Virus (HBV) core protein;
   a drug captured in said capsid; and
   a lipid envelope covalently attached to said capsid, thereby enveloping said capsid.

2. The self-assembling nanoparticle drug delivery system of claim 1 wherein said HBV core protein is mutated such that at least one amino acid of SEQ ID NO. 1 or SEQ ID NO. 2 selected from the group consisting of phenylalanine 23, aspartic acid 29, threonine 33, leucine 37, valine 120, valine 124, arginine 127, tyrosine 132, glutamic acid 77, aspartic acid 78 and alanine 80 is changed to a cysteine.

3. The self-assembling nanoparticle drug delivery system of claim 1 wherein said lipid envelope comprises phospholipids.

4. The self-assembling nanoparticle drug delivery system of claim 3 wherein said phospholipids are selected from the group consisting of phosphotidyl ethanolamine, phosphatidyl glycerol and hydrogenated soy phosphatidylcholine.

5. The self-assembling nanoparticle drug delivery system of claim 1, wherein said HBV core protein has the amino acid sequence of SEQ ID NO. 1 or SEQ ID NO. 2.

6. The self-assembling nanoparticle drug delivery system of claim 1, wherein said drug is selected from the group consisting of peptides, proteins, nucleic acids and small molecule synthetic chemical drugs.

7. The self-assembling nanoparticle drug delivery system of claim 1 further comprising at least one of a cholesterol-tagged polyethylene glycol, and a polyethylene glycol-phospholipid.

8. The method of claim 1 wherein said lipid envelope is covalently attached to said capsid though a maleimide intermediate.

9. A self-assembling nanoparticle drug delivery system comprising:
   a capsid comprised of non-replicating viral capsid protein, wherein said viral capsid protein comprises a modified Hepatitis B Virus (HBV) core protein;
   a drug captured in said capsid; and
   a lipid envelope covalently attached to said capsid through a maleimide intermediate, thereby enveloping said capsid.

10. The self-assembling nanoparticle drug delivery system of claim 1 wherein said lipid envelope comprises phosphatidyl glycerol, hydrogenated soy phosphatidylcholine, and cholesterol.

11. The self-assembling nanoparticle drug delivery system of claim 2, wherein the glutamic acid at amino acid 77 of SEQ ID NO. 1 or SEQ ID NO. 2 is changed to a cysteine.

12. The self-assembling nanoparticle drug delivery system of claim 11 wherein phosphatidyl-ethanolamine maleimide is attached to the cysteine at amino acid 77 of SEQ ID NO. 1 or SEQ ID NO. 2.

13. The self-assembling nanoparticle drug delivery system of claim 9, wherein the HBV core protein is selected from the group consisting of SEQ ID NO: 1 and SEQ ID NO: 2, wherein the glutamic acid at amino acid 77 is changed to a cysteine in said SEQ ID NO: 1 or SEQ ID NO: 2.

14. The self-assembling nanoparticle drug delivery system of claim 9, wherein the HBV core protein is mutated such that at least one amino acid of SEQ ID NO: 1 or SEQ ID NO 2 selected from the group consisting of phenylalanine 23, aspartic acid 29, threonine 33, leucine 37, valine 120, valine 124, arginine 127, tyrosine 132, glutamic acid 77, aspartic acid 78 and alanine 80 is changed to a cysteine.

15. A self-assembling nanoparticle drug delivery system comprising:

a capsid comprised of non-replicating viral capsid protein, wherein said viral capsid protein is a modified Hepatitis B Virus (HBV) core protein comprising the amino acid sequence of SEQ ID NO: 2, wherein the glutamic acid at amino acid 77 is changed to a cysteine;

a drug captured in said capsid; and a lipid envelope covalently attached to said capsid by a phosphatidyl-ethanolamine maleimide to the cysteine at amino acid 77 of SEQ ID NO: 2, thereby enveloping said capsid.

* * * * *